United States Patent [19]

Gray et al.

[11] Patent Number: 4,672,125

[45] Date of Patent: Jun. 9, 1987

[54] CHLORINATION OF β-METHYLPYRIDINE COMPOUNDS

[75] Inventors: Trevor E. Gray, Walnut Creek; Charles B. Grant, Pittsburg; Thomas J. Dietsche, Berkely, all of Calif.

[73] Assignee: The Dow Chemical Company, Midland, Mich.

[21] Appl. No.: 808,779

[22] Filed: Dec. 13, 1985

[51] Int. Cl.$^4$ .............................................. C07D 213/26
[52] U.S. Cl. ..................................... 546/345; 546/346
[58] Field of Search ........................................ 546/345

[56] References Cited

U.S. PATENT DOCUMENTS 2,516,402 7/1950 McBee et al. ........................ 546/345
2,695,902 11/1954 Wilson et al. ........................ 546/345
4,225,716 9/1980 Bühler et al. ........................ 546/345

OTHER PUBLICATIONS

Keith B. Dillon et al., Chem. Soc., London, pp. 1410–1416, 1977.
Kimbrough, Jr., et al. 1969, J. Organ. Chem., vol. 34, pp. 3655–3656.
S. J. Davis et al., 1962, Chem. Soc., London, pp. 3638–3644.

Primary Examiner—Alan L. Rotman
Assistant Examiner—Robert C. Whittenbaugh
Attorney, Agent, or Firm—Joseph T. Majka; Ronald G. Brookens

[57] ABSTRACT

A method is disclosed for preparing a chlorinated β-methylpyridine by chlorinating a β-methylpyridine compound with $PCl_5$ in the presence of phenylphosphonic dichloride.

6 Claims, No Drawings

CHLORINATION OF β-METHYLPYRIDINE COMPOUNDS

FIELD OF THE INVENTION

This invention relates to a novel process for chlorinating β-methylpyridine compounds.

BACKGROUND OF THE INVENTION

Processes for chlorinating β-methylpyridine compounds are known employing conventional vapor phase and liquid phase chlorination procedures. Vapor phase chlorination processes require that the starting materials are reacted together in a vapor phase and have the disadvantage of high energy requirements to effect the chlorination of the β-methylpyridine compounds. This type of process also appears to have a low capability for selectively chlorinating the β-methyl moiety. Vapor phase chlorination is also an impractical procedure for chlorinating many hydroxypyridine compounds due to the low vapor pressure of these compounds.

In liquid phase chlorination processes, the starting materials are reacted together in a liquid phase. Known liquid phase processes lack the capability to selectively chlorinate both the hydroxyl and β-methylpyridine moieties of hydroxy-β-methylpyridine compounds, since known liquid phase processes tend to favor chlorination of hydrogen on the pyridine ring over chlorination of hydroxyl moieties on the ring. Further, such liquid phase chlorination processes also have the disadvantage in requiring multiple steps to effect the desired chlorination of the pyridine compound.

SUMMARY OF THE INVENTION

Chlorinated β-methylpyridine compounds of the formula

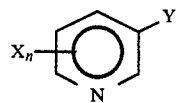

(I)

wherein
X is chloro;
n is 1, 2, 3 or 4 and
Y is $CH_3$, $CH_2Cl$, $CHCl_2$ or $CCl_3$ are made by contacting phosphorous pentachloride, in the presence of phenylphosphonic dichloride ($C_6H_5POCl_2$), with a β-methylpyridine compound of the formula:

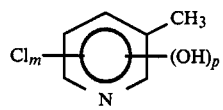

(II)

wherein
m is 0, 1, 2, 3 or 4;
p is 0, 1, 2, 3 or 4;
m +p = 1, 2, 3 or 4; and recovering said chlorinated β-methylpyridine compound.

The chlorinated β-methylpyridine compounds are useful as intermediates used in making pesticides, especially herbicides and insecticides. In other applications, the process of the present invention is also useful in preparing chlorinated β-methylpyridine compounds which can be employed as standards in monitoring the yield and purity of products derived from commercial processes for making chlorinated β-methylpyridine compounds.

Preferred chlorinated β-methylpyridine compounds of Formula (I) prepared by the present method include 3-(trichloromethyl)pyridine, 3-chloromethyl2,4,6-trichloropyridine, 3-dichloromethyl-2,4,6-trichloropyridine and 2,4,5,6-tetrachloro-3-chloromethylpyridine.

DETAILED DESCRIPTION OF THE INVENTION

The β-methylpyridine compounds of Formula II may be advantageously reacted with phosphorus pentachloride at temperatures ranging from 70° C. to about 250° C., preferably from about 100° C. to about 225° C., more preferably from about 160° to about 200° C. Generally, as the temperature is increased, the rate of chlorination is increased.

Phosphorus pentachloride ($PCl_5$) is a compound well known to those skilled in the art and is available commercially.

Phenylphosphonic dichloride ($C_6H_5POCl_2$) is a well-known compound and is also commercially available. Phenylphosphonic dichloride is believed to serve as a catalyst, reactant and solvent in the chlorination of β-methyl pyridine and is essential for the preparation of the compounds of Formula I. Phenylphosphonic dichloride has a melting point of 3° C. and a boiling point of 258° C. at 760 mm Hg.

The resulting reaction mixture is usually maintained, with stirring, for a period of time sufficient to provide for substantial completion of the reaction. Generally, the reaction is complete in a period from about 0.5 hours to about 5 hours or more. Also, as the time for reaction is increased, the rate of chlorination is increased.

The reaction can be conducted in the presence of a solvent. Representative solvents include the chlorinated hydrocarbon solvents, such as carbon tetrachloride, perchloroethylene and chlorobenzene. Preferably, phenylphosphonic dichloride acts as the solvent as indicated above. When the molar ratio of $PCl_5$:β-methylpyridine is greater than 3:1 the phosphorus pentachloride which would otherwise be used as a reactant, performs as a solvent. The reaction can be also conducted neat, i.e., in the absence of a solvent.

In the preparation of the chlorinated β-methylpyridine compounds of Formula I, the β-methylpyridine compound of Formula II is reacted with the phosphorus pentachloride in a range molar ratio between about 10:1 to about 1:1 (phosphorus pentachloride:β-methylpyridine), preferably in a molar ratio of 2:1, most preferably in a molar ratio of 1.1:1 per chlorine to be added to the compound of Formula II.

Phenylphosphonic dichloride ($\phi POCl_2$) can be advantageously reacted with the β-methylpyridine compound of Formula II in a molar ratio ranging between 2:1 and 50:1 (phenylphosphonic dichloride:β-methylpyridine compound), preferably in a molar ratio between about 3:1 to about 6:1.

After the completion of the reaction, the desired chlorinated β-methylpyridine thus formed is recovered using conventional recovery procedures, such as extraction with organic solvents. In typical procedures, after the reaction has been terminated, the reaction mixture is quenched, washed with water and then extracted with organic solvents such as diethylether, chlorinated hydrocarbons, aromatic or hydrocarbon compounds. Representative chlorinated hydrocarbons include chloroform, methylene chloride, perchloroethylene and carbon tetrachloride. Representative aromatic solvents used for recovery include benzene, toluene and xylene. Representative hydrocarbons include hexane or heptane. Most preferably, the extraction solvents are the chlorinated hydrocarbons.

Where desired, the reaction mixture containing the organic solvents and/or aqueous washes can be advantageously filtered. After partitioning the organic phase from the aqueous phase, the organic phase can be dried over known drying agents, including sodium sulfate ($Na_2SO_4$), magnesium sulfate ($MgSO_4$) or calcium chloride ($CaCl_2$) The chlorinated $\beta$-methylpyridine compounds are recovered using conventional purification procedures such as solvent evaporation, distillation, recrystallization and filtration.

The following examples are prepared to illustrate preparation of typical compounds of the present invention, but the scope of the invention is not to be considered limited to the specific examples given.

EXAMPLE 1

To a flask containing 300 grams (g) of phenylphosphonic dichloride ($\phi POCl_2$) was added 51.6 g of 2-chloro-4,6-dihydroxy-3-methylpyridine (0.32 mole). The flask was heated to a temperature of 100° C. after which 263 g of phosphorus pentachloride ($PCl_5$) was slowly added to the reaction mixture. After addition of the $PCl_5$, the flask was heated to 110° C. to distill off phosphorus oxychloride ($POCl_3$), a by-product of the reaction. The heat was raised to bring the temperature of the reaction mixture to 190° C. and this temperature was maintained for 3 hours. The flask was then removed from the heat, allowed to cool to room temperature and the reaction mixture was poured into a 4 liter (1) beaker containing ice. The reaction mixture in the ice was extracted with diethylether, evaporated and recrystallized with heptane and recrystallized again with water:ethanol (15:85 v/v) to yield a brown, crystalline solid. A gas chromatographic-mass spectrographic (GC-MS) and a nuclear magnetic resonance (NMR) analysis of the brown solid showed it to contain 3-chloromethyl-2,4,6-trichloropyridine. Following a further recrystallization from ethanol (1 g solid:5 ml ethanol), a gas-chromatographic (GC) analysis of the recrystallized solid showed it to contain 78.2 percent of 3-chloromethyl-2,4,6-trichloropyridine, 7.7 percent of 3-chloromethyltetrachloropyridine, 5.0 percent of 3-methyl-2,4,6-trichloropyridine and 2.8 percent of 3-dichloromethyl-2,4,6-trichloromethylpyridine.

EXAMPLE 2

To a flask containing 466 g of phenylphosphonic dichloride (2.38 moles) was added 100 g of 2-chloro-4,6-dihydroxy-3-methylpyridine (0.63 moles). The flask was heated to a temperature of 80° C. after which 600 g of $PCl_5$ was slowly added to the reaction mixture. After addition of the $PCl_5$ the flask was heated to a temperature of 140° C. for 45 minutes, during which phosphorus oxychloride ($POCl_3$) was observed to distill off the reaction mixture. The flask was then heated to a temperature of 180° C. and maintained at that temperature for 5 hours. After cooling overnight to room temperature, the reaction mixture was poured into a beaker of cracked ice and the reaction mixture was made alkaline by the addition of aqueous sodium hydroxide (NaOH). After the reaction mixture had cooled, diethylether was mixed with the reaction mixture. The diethylether and water(aqueous) phases were allowed to partition over a period of two days after which the aqueous phase was separated and saved. Subsequent extraction of this saved aqueous phase with diethylether and evaporation of the diethylether yielded 4 g of residue. More water was added to the diethylether phase which had been separated and the ether aqueous phases were cooled overnight in an ice bath. Black solid materials which did not dissolve either in the aqueous or in the diethylether phase was discarded. The aqueous and diethylether phases were suction filtered through a coarse fritted filter, additional water was added and a resulting black diethylether phase was separated from the aqueous phase. Sodium sulfate ($Na_2SO_4$) was added to the black diethylether phase, causing a clear aqueous phase to partition from the black diethylether phase. The aqueous phase was removed, the black diethylether phase was dried over $Na_2SO_4$ and the solvent was evaporated off with a rotary evaporator, to yield 43 g of a tarry black residue. This residue was added to the 4 g of residue extracted as described hereinabove to give a total yield of 47 g (43 g +4 g) residue. Analysis of the residue by gas chromatography showed it to contain, on an area percentage basis, 56.0 percent 3-chloromethyl-2,4,6-trichloropyridine, 16.6 percent 3-dichloromethyl-2,4,6-trichloropyridine, 6.5 percent 3-chloromethyltetrachloropyridine and 14.9 percent 3-methyl-2,4,6-trichloropyridine. The above compounds were further purified by conventional distillation procedures.

EXAMPLE 3

To a flask containing 600 g of phenyl phosphonic dichloride (3.09 moles) was added 60.4 g of 3-methylpyridine (0.6 moles). The flask was heated to a temperature of 100° C. after which 504.6 g of phosphorous pentachloride was slowly added to the reaction mixture. After addition of the phosphorous pentachloride the flask was heated to 110° C. to distill off phosphorous oxychloride ($POCl_3$), a by-product of the reaction. The temperature of the reaction mixture was then raised to 170° C. and maintained at this temperature for 2 hours. The flask was cooled to room temperature and left undisturbed for 1 week. After one week, the flask was reheated to a temperature of 170° C. for 4 hours and cooled to room temperature. The next day, the flask was reheated to 170° C., sampled after 5 hours and analyzed. The analysis of the reaction mixture by capillary gas-liquid chromatography showed it to contain, on an area percentage basis:

(1) 7.3% 3-trichloromethyl-5-chloropyridine,
(2) 59.7% 3-trichloromethyl-6-chloropyridine,
(3) 13.8% 3-trichloromethyl-4,6-dichloropyridine,
(4) 1.4% 3-trichloromethyl-5,6-dichloropyridine,
(5) 1.7% 3-trichloromethy-2,6-dichloropyridine,
(6) 0.3% 3-monochloromethyl-2,4,6-trichloro pyridine,
(7) 0.9% 3-trichloromethyl-4,5,6-trichloropyridine, and
(8) 14.9% Unresolved.

The identity of the following compounds was also confirmed by gas-chromatographic infra-red spectroscopy(GC-IR): (2), (3), (5) and (7). Also, the identity of the following compound was determined by GC-IR but not by capillary GC: 3-dichloromethyl-6-chloropyridine.

By following the preparative procedures as set forth in the above examples and employing the appropriate starting reactants, the following compounds are prepared, as set forth in Table 1.

TABLE 1

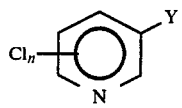

| Example Number | n | Chlorine Position | Y |
|---|---|---|---|
| 4 | 4 | (2,4,5,6) | CHCl$_2$ |
| 5 | 4 | (2,4,5,6) | CH$_2$Cl |
| 6 | 3 | (2,5,6) | CCl$_3$ |
| 7 | 3 | (2,4,6) | CH$_2$Cl |
| 8 | 3 | (2,4,6) | CHCl$_2$ |
| 9 | 3 | (4,5,6) | CH$_2$Cl |
| 10 | 3 | (4,5,6) | CHCl$_2$ |
| 11 | 2 | (4,6) | CHCl$_2$ |
| 12 | 2 | (4,6) | CH$_2$Cl |
| 13 | 2 | (5,6) | CHCl$_2$ |
| 14 | 2 | (5,6) | CH$_2$Cl |
| 15 | 2 | (5,6) | CCl$_3$ |
| 16 | 2 | (2.6) | CCl$_3$ |
| 17 | 1 | (4) | CH$_2$Cl |
| 18 | 1 | (4) | CH$_2$Cl |
| 19 | 1 | (6) | CHCl$_2$ |
| 20 | 1 | (6) | CH$_2$Cl |
| 21 | 1 | (6) | CCl$_3$ |

PREPARATION OF STARTING MATERIALS

The β-methylpyridine compounds of Formula II, for the most part, are known to those skilled in the art. The following references illustrate representative preparations of selected hydroxy-β-methylpyridines.

The compounds 2-hydroxy-5-methylpyridine and 5-methyl-2(1H)-pyridinone are disclosed in W. Herz and D. R. K. Murty, J. Org. Chem., 26, 122 (1961).

The compounds 3-hydroxy-5-methylpyridine and 5-methyl-3-pyridinol are disclosed in S. Okuda and M. M. Robison, J. Amer. Chem. Soc., 81, 740 (1959).

The compounds 2-chloro-5-hydroxy-3-methylpyridine and 6-chloro-3-methyl-3-pyridinol are disclosed in J. Nemec, F. S. Meeker, and E. C. Schreiber, J. Heterocyclic Chem., 11, 569 (1974).

U.S. Pat. No. 4,374,140, discloses the preparation of 2-chloro-5-hydroxy-3-methylpyridine.

The compounds 4-hydroxy-3-methylpyridine, 3-methyl-4-pyridinol and 3-methyl-4-(1H)-pyridinone are disclosed in E. C. Taylor and J. S. Driscoll, J. Org. Chem., 26, 3001 (1961).

The compounds 2-hydroxy-3-methylpyridine, 3-methyl-2-pyridinol and 3-methyl-2(1H)-pyridinone are disclosed in CAS Nos. 91914-04-4 and 1003-56-1, Beilstein, 2nd Supplement, vol. 21, pg. 36.

The compounds 5-chloro-2-hydroxy-3-methylpyridine, 5-chloro-3-methyl-2-pyridinol and 5-chloro-3-methyl-2(1H)-pyridinone are disclosed in M. P. Cava and N. K. Bhattacharya, J. Org. Chem., 23, 1614 (1958).

The compounds 2,4-dihydroxy-5-methylpyridine, 5-methyl-2,4-pyridinediol, 4-hydroxy-5-methyl-2(1H)pyridinone and 5-methyl-2,4(1H,3H)-pyridinedione, are disclosed in S. Nesnow, T. Miyazaki, T. Khwaja, R. B. Meyer, Jr., and C. Heidelberger, J. Med. Chem., 16, 524 (1973).

The compounds 6-chloro-2,4-dihydroxy-5-methylpyridine, 6-chloro-5-methyl-2,4-pyridinediol, 6-chloro-4-hydroxy-5-methyl-2(1H)-pyridinone, and 6-chloro-5-methyl-2,4(1H,3H)-pyridinedione are disclosed in S. J. Davis, J. A. Elvidge, and A. B. Foster, J. Chem. Soc., 1962 3638.

The compounds 2,6-dihydroxy-3-methylpyridine, 6-hydroxy-3-methyl-2(1H)-pyridinone and 3-methyl-2,6-pyridinediol, are disclosed in U. Horn, F. Mutterer, and C. D. Weis, Helv. Chim. Acta, 59, 190 (1976).

The compounds 3,4-dihydroxy-5-methylpyridine, 5-methyl-3,4-pyridinediol and 3-hydroxy-5-methyl-4(1H)pyridinone, are disclosed in Japan Kokai Tokkyo Koho, JP 59,161,359 (to Tokuyama Soda Co., Ltd.) (Chem. Abstr. 102, 113315).

The compounds 3-methyl-2,5,6-trihydroxypyridine, -methyl-2,3,6-pyridinetriol and 6-hydroxy-5-methyl-2,3-(1H, 4H)-pyridinedione are disclosed in H. J. Knackmuss, Chem. Ber., 101, 2679 (1968).

The compounds 3-methyl-2,4,6-trihydroxypyridine, 3-methyl-2,4,6-pyridinetriol and 6-hydroxy-3-methyl-2,4-(IH, 3H)-2,4-pyridinedione are disclosed in Beilstein, vol. 21, pg. 198.

General teachings as to preparation of pyridones can be found in Pyridine and its Derivatives, Vol. 14, Suppl. Part 3, R.A. Abramovitch (ed.), John Wiley & Sons, Chapter XII, pages 597–1180.

We claim:

1. A method for preparing a chlorinated β-methylpyridine compound of the formula:

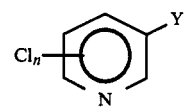

wherein
n is 1, 2, 3 or 4, and
Y is CH$_3$, CH$_2$Cl, CHCl$_2$ or CCl$_3$
which comprises contacting phosphorous pentachloride, in the presence of phenylphosphonic dichloride (C$_6$H$_5$POCl$_2$) with a β-methylpyridine compound of the formula wherein
m is 0, 1, 2, 3 or 4;
p is 0, 1, 2, 3 or 4;
m+p=1, 2, 3 or 4; and recovering said chlorinated β-methylpyridine compound.

2. The method of claim 1 wherein said chlorinated β-methylpyridine is 3-chloromethyl-2,4,6-trichloropyridine.

3. The method of claim 1 wherein said chlorinated β-methylpyridine is 3-dichloromethyl-2,4,6-trichloropyridine.

4. The method of claim 1 wherein said chlorinated β-methylpyridine is 3-methyl-2,4,6-trichloropyridine.

5. The method of claim 1 wherein said chlorinated β-methylpyridine is 3-chloromethyltetrachloropyridine.

6. The method of claim 1 wherein said hydroxy β-methylpyridine compound is 2-chloro-4,6-dihydroxy-3-methylpyridine.

* * * * *